United States Patent [19]

Benedict et al.

[11] Patent Number: 4,661,341

[45] Date of Patent: Apr. 28, 1987

[54] ORAL COMPOSITIONS

[75] Inventors: James J. Benedict, Norwich, N.Y.; Richard J. Sunberg, Oxford, Ohio

[73] Assignee: The Procter & Gamble Company, Cincinnati, Ohio

[21] Appl. No.: 781,595

[22] Filed: Sep. 30, 1985

Related U.S. Application Data

[63] Continuation-in-part of Ser. No. 666,397, Oct. 30, 1984, abandoned.

[51] Int. Cl.$^4$ ................................................ A61K 7/16
[52] U.S. Cl. ........................................ 424/48; 424/81; 424/49
[58] Field of Search ................................ 424/48–58, 424/81

[56] References Cited

U.S. PATENT DOCUMENTS

| | | | |
|---|---|---|---|
| 2,941,926 | 6/1960 | Salzmann et al. | 424/57 |
| 2,975,102 | 3/1961 | Matsumura et al. | 424/49 |
| 3,137,632 | 6/1964 | Schiraldi | 167/93 |
| 3,429,963 | 2/1969 | Shedlovsky | 424/56 |
| 3,678,154 | 7/1972 | Widder et al. | 424/52 |
| 3,737,522 | 6/1973 | Francis | 424/49 |
| 3,956,480 | 5/1976 | Dichter et al. | 424/49 |
| 4,183,914 | 1/1980 | Gaffar et al. | 424/49 |
| 4,217,342 | 8/1980 | Gaffar et al. | 424/49 |
| 4,217,343 | 8/1980 | Gaffar et al. | 424/49 |
| 4,254,101 | 3/1981 | Denny, Jr. | 424/49 |
| 4,296,096 | 10/1981 | Pierce | 424/52 |
| 4,304,766 | 12/1981 | Chang | 424/52 |
| 4,482,535 | 11/1984 | Sugar et al. | 424/49 |

FOREIGN PATENT DOCUMENTS 721898 9/1972 South Africa .

Primary Examiner—Shep K. Rose
Attorney, Agent, or Firm—Richard C. Witte; John V. Gorman; Douglas C. Mohl

[57] ABSTRACT

Oral compositions containing as an anticalculus agent an acrylic acid polymer or copolymer having a mass average molecular weight of from about 3500 to about 7500 are described herein.

15 Claims, No Drawings

ORAL COMPOSITIONS

CROSS REFERENCE TO RELATED APPLICATION

This is a continuation-in-part of our co-pending application having Ser. No. 666,397, filed Oct. 30, 1984, now abandoned.

TECHNICAL FIELD

The present invention relates to oral compositions such as liquid dentifrices, toothpastes and mouthwashes, which provide an anticalculus benefit.

BACKGROUND OF THE INVENTION

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. In addition to being unsightly and undesirable from an aesthetic standpoint, the mature calculus deposits are regarded by many as a constant source of mechanical irritation of the gingiva.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ion and/or crystal growth inhibition which prevents the calculus from forming and/or breaks down mature calculus by removing calcium.

The prior art discloses a number of chelating agents for this purpose. British Pat. No. 490,384, Feb. 15, 1937, discloses oral compositions containing ethylenediaminetetraacetic acid, nitrilotriacetic acid and related compounds as anticalculus agents. U.S. Pat. No. 3,678,154, July 18, 1972 to Widder et al. discloses oral compositions containing certain polyphosphonates and fluoride. U.S. Pat. No. 3,737,533, June 5, 1973 to Francis discloses oral compositions containing certain carbonyl diphosphonates.

In addition to the above references, the prior art discloses dentifrices and mouthwashes containing soluble pyrophosphate salts which have been included for a variety of purposes. Included among such references are U.S. Pat. No. 2,941,926, June 21, 1960 to Salzmann et al. which discloses dental powders containing chlorophyll and pyrophosphate salts. U.S. Pat. No. 3,137,632, June 16, 1964 to Schiraldi discloses toothpastes containing pyrophosphate salts. U.S. Pat. Nos. 3,927,201 and 202, Dec. 16, 1975 to Baines et al. and Harvey et al., respectively, disclose toothpastes which utilize soluble pyrophosphates as abrasives. U.S. Pat. Nos. 4,244,931, Jan. 13, 1981 and 4,247,526, Jan. 27, 1981 to Jarvis et al. disclose pyrophosphate salts in dicalcium phosphate systems. Jap. Patent Application Disclosure No. 4945-1974 discloses soluble pyrophosphates in a variety of dentifrice systems. U.S. Pat. No. 4,333,551, Apr. 6, 1982 to Parran discloses tetraalkali metal salts in mouthwash compositions.

In addition to the use of the above mentioned materials the use of certain acrylic acid polymers and other agents have also been disclosed for use as anticalculus agents. Included among such agents are polyelectrolytes such as copolymers of maleic anhydride and ethylene disclosed in U.S. Pat. No. 3,429,963, Feb. 25, 1969 to Shedlovsky. Shedlovsky also discloses polyacrylic acid having an average molecular weight of 1500 and greater. Other references disclosing polyacrylic acids in oral compositions are South African Pat. No. 720898, Sept. 12, 1972 which discloses such acids having a molecular weight of from 1000 to 2,000,000; and U.S. Pat. No. 4,304,766, Dec. 8, 1971 to Chang discloses polyacrylic acid having a molecular weight in the range of 2,000 to 4,000,000 for use as a membrane to prevent the elution from teeth of previously applied agents. Finally U.S. Pat. No. 3,956,480, May 11, 1976 discloses complexes of anionic polymers (e.g., acrylic acid) and a cationic therapeutic agent (e.g., chlorhexidine) as anticalculus agents.

In spite of the many disclosures in the anticalculus area, the need for improved anticalculus products still exist. The prior art, while suggesting the use of polyacrylic acid polymers or copolymers in oral compositions, does not suggest the need for using such uncomplexed polymers within a particular molecular weight range to achieve maximum anticalculus efficacy.

It is an object of the present invention to provide compositions which deliver an effective anticalculus benefit.

It is a further object of the present invention to provide an effective anticalculus product utilizing polyacrylic acid polymers or copolymers having a mass average molecular weight of from about 3500 to about 7500.

It is a further object of the present invention to provide an anticalculus product which does not inhibit remineralization of the teeth.

It is still a further object of the present invention to provide an effective method for treating calculus.

It is still a further object of the present invention to provide compositions which are cosmetically acceptable.

These and other objects will become more clear from the detailed description which follows.

All percentages and ratios used herein are by weight unless otherwise specified.

SUMMARY OF THE INVENTION

The present invention embraces an oral composition comprising:

(a) a safe and effective amount of a polyacrylic acid polymer or copolymer having a mass average molecular weight of from about 3500 to about 7500; and (b) a pharmaceutically acceptable carrier.

The present invention also encompasses a method for retarding the development of dental calculus.

DETAILED DESCRIPTION OF THE INVENTION

The compositions of the present invention comprise particular polyacrylic acid polymers or copolymers and a pharmaceutically acceptable carrier.

By "safe and effective amount" as used herein, means sufficient compound to reduce calculus while being safe to the hard and soft tissues of the oral cavity.

By the term "comprising", as used herein, is meant that various additional components can be conjointly employed in the compositions of this invention as long as the polyacrylic acid polymer or copolymer performs its intended functions.

By the term "carrier", as used herein, is meant a suitable vehicle which is pharmaceutically acceptable and can be used to apply the present compositions in the oral cavity.

Polyacrylic Acid

The anticalculus agent useful in the compositions of the present invention are polyacrylic acid polymers or copolymers having a mass average molecular weight of from about 3500 to about 7500.

Polyacrylic acid polymers are staple items of commerce and are made by polymerizing acrylic acid,

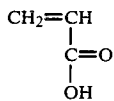

to form the repeating chain

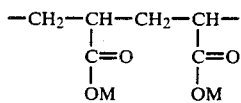

the repetition being sufficient to provide the molecular weight desired. M may be an alkali metal or ammonium ion or hydrogen. Polymers of the type useful in the present invention are available from Rohm and Haas Company.

Copolymers of acrylic acid and other monomers may also be used in the present invention. Suitable other monomers include methacrylic acid, 2-hydroxypropyl acrylate, 3-hydroxypropyl methacrylate, 3-hydroxy propyl acrylate and acrylamide. It is preferred that with methacrylic acid, the number of acrylic acid units in the polymer be at least 50% of the total units present. With other monomers it is preferred that the percentage be at least 80%. Mixtures of other monomers may also be used.

While the molecular weight may be in the range of about 3500 to about 7500, preferably the molecular weight is from about 4000 to about 5500, most preferably from about 4300 to about 5200. A particularly preferred material is a polyacrylic acid polymer having a molecular weight of about 4500 which can be provided by Rohm and Haas carrying the identification LMW-45.

The amount of the polymer used in the present compositions is generally from about 2.5% to about 20%, preferably from about 3% to about 10%, most preferably from about 4% to about 8%. Mixtures of polyacrylic acid polymers or copolymers are also useful in the present invention.

Pharmaceutically Acceptable Carrier

The carrier for the polyacrylic acid polymer or copolymer can be any vehicle suitable for use in the oral cavity. Such carriers include the usual components of mouthwashes, toothpastes, tooth powders, prophylaxis pastes, lozenges, gums and the like and are more fully described hereinafter. Dentifrices and mouthwashes are the preferred systems.

The abrasive polishing material contemplated for use in the present invention can be any material which does not excessively abrace dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, June 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, July 29, 1982, incorporated herein by reference.

The abrasive in the compositions described herein is present at a level of from about 6% to about 70%, preferably from about 15% to about 25% when the dentifrice is a toothpaste. Higher levels, as high as 90%, may be used if the composition is a toothpowder.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable surfactants are disclosed by Gieske et al. in U.S. Pat. No. 4,051,234, Sept. 27, 1977, incorporated herein by reference.

It is common to have a water-soluble fluoride compound present in dentifrices in an amount sufficient to give a fluoride concentration of from about 0.0025% to about 5.0% by weight, preferably from about 0.005% to about 2.0% by weight, to provide additional anticaries effectiveness. Preferred fluorides are sodium fluoride, stannous fluoride, indium fluoride, and sodium monofluorophosphate. Norris et al., U.S. Pat. No. 2,946,735, issued July 26, 1960 and Widder et al., U.S. Pat. No. 3,678,154, issued July 18, 1972 disclose such salts as well as others.

Water is also present in the toothpastes of this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that wnhich is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

Another preferred embodiment of the present invention is a mouthwash composition. Conventional mouthwash composition components can comprise the carrier for the antimicrobial of the present invention. Mouthwashes generally comprise from about 20:1 to about 2:1 of a water/ethyl alcohol solution and preferably other ingredients such as flavor, sweeteners, humectants and sudsing agents such as those mentioned above for dentifrices. The humectants, such as glycerin and sorbitol give a moist feel to the mouth. Generally, on a weight basis the mouthwashes of the invention comprise 5% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably 0.03% to 0.3%) flavoring agent, and the balance water. The amount of antimicrobial agent in mouthwashes is typically from about 0.01 to about 0.5% by weight.

Suitable lozenge and chewing gum components are disclosed in U.S. Pat. No. 4,083,955, Apr. 11, 1978 to Grabenstetter et al., incorporated herein by reference.

The pH of the present compositions and/or its pH in the mouth can be any pH wnhich is safe for the mouth's hard and soft tissues. Such pH's are generally from about 3 to about 10, preferably from about 4 to about 8.

METHOD OF MANUFACTURE

The carrier compositions of the present invention can be made using methods which are common in the oral products area.

For example toothpaste compositions may be prepared by mixing part of the humectant and water together and heating to 66°–71° C. The fluoride source, if present, is then added along with the sweetener, the polyacrylic acid polymer or copolymer, the opacifier and the flavor. To this mixture is added the abrasive which is mixed in well. The thickener is then slurried with the remainder of the humectant and milled prior to being added to the other components.

COMPOSITION USE

The present invention in its method aspect involves applying to the oral cavity safe and effective amounts of the polyacrylic acid polymer or copolymer. Generally an amount of at least about 0.025 grams of the polymer is effective.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLE I

The following composition is representative of the present invention.

| Component | Weight % |
| --- | --- |
| Sorbitol (70% aqueous solution) | 35.000 |
| Water | 14.771 |
| PEG-6[1] | 1.000 |
| Silica Dental Abrasive[2] | 20.000 |
| Sodium Fluoride | 0.243 |
| Titanium dioxide | 0.500 |
| Sodium saccharin | 0.286 |
| Sodium alkyl sulfate (27.9% aqueous solution) | 4.000 |
| Flavor | 1.040 |
| Carboxyvinyl Polymer[3] | 0.300 |
| Carrageenan[4] | 0.800 |
| Polyacrylic acid[5] (34% aqueous solution) | 22.060 |
| | 100.000 |

[1] PEG-6 - Polyethylene glycol having molecular weight of 600.
[2] Precipitated silica identified as Zeodent 119 offered by J. M. Huber.
[3] Carbopol offered by B. F. Goodrich Company.
[4] Iota Carrageenan offered by Hercules Chemical Company
[5] Polyacrylic acid polymer having a mass average molecular weight of about 4500 offered by Rohm and Hass.

EXAMPLE II

This composition is another example of the present invention.

| Component | Weight % |
| --- | --- |
| Sorbitol as in Example I | 35.000 |
| Water | 15.073 |
| Sodium Fluoride | 0.243 |
| PEG-6 | 1.000 |
| Carrageenan | 0.800 |
| Sodium saccharin | 0.280 |
| Titanium dioxide | 0.500 |
| Flavor | 1.044 |
| Silica Dental Abrasive as in Example I | 20.000 |
| Sodium alkyl sulfate as in Example I | 4.000 |
| Polyacrylic acid (34%) as in Example I | 22.060 |
| | 100.000 |

The compositions of Example I and II are effective anticalculus products as well as cosmetically acceptable.

In the above compositions the abrasive may be replaced by other abrasives such as calcium carbonate, calcium pyrophosphate, tricalcium phospate, dicalcium othophosphate dihydrate and hydrated alumina with similar results obtained. Similarly other thickeners such as gum arabic and carboxymehyl cellulose may be used as well as other fluoride sources such as stannous fluoride, potassium fluoride, indium fluoride, zinc fluoride and sodium monofluorophosphate. Silicas are the preferred abrasives when fluoride sources are used in the compositions. Other acrylic acid polymers or copolymers having molecular weights in the range of about 3500 to about 7500 may also be used in place of the 4500 molecular weight material.

EXAMPLE III

The following mouthwash composition is another composition of the present invention.

| Component | Weight % |
|---|---|
| SDA 40 Alcohol | 8.00 |
| Flavor | 0.08 |
| Emulsifier | 0.08 |
| Sodium Fluoride | 0.05 |
| Glycerin | 10.00 |
| Sweetener | 0.02 |
| Benzoic acid | 0.05 |
| Sodium hydroxide | 0.20 |
| Dye | 0.04 |
| Water | 66.78 |
| Polyacrylic acid (34%) as in Example I | 14.70 |
| | 100.00 |

EXAMPLE IV

The following is a lozenge composition of the present invention.

| Component | Weight % |
|---|---|
| Sorbitol | 17.5 |
| Mannitol | 17.5 |
| Starch | 13.6 |
| Sweetener | 1.2 |
| Flavor | 11.7 |
| Color | 0.1 |
| Polyacrylic acid (34%) as in Example I | 12.8 |
| Corn syrup | balance |

EXAMPLE V

The following is a chewing gum composition of the present invention.

| Component | Weight % |
|---|---|
| Sorbitol crystals | 38.44 |
| Paloja-T gum base[1] | 20.00 |
| Sorbitol (70% Aqueous solution) | 20.00 |
| Mannitol | 10.00 |
| Glycerin | 7.56 |
| Flavor | 1.00 |
| Polyacrylic acid as in Example I | 3.00 |
| | 100.00 |

[1]Supplied by L. A. Dreyfus Company

The compositions of Examples III, IV and V are also effective anticalculus products and are cosmetically acceptable.

What is claimed is:

1. An oral composition effective in reducing calculus comprising:
   (a) a safe and effective amount of an anticalculus agent selected from the group consisting of polyacrylic acid polymers,

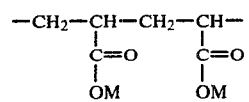

copolymers of acrylic acid and another monomer and mixtures thereof; and
   (b) a pharmaceutically acceptable carrier selected from the group consisting of toothpastes, mouthwashes, chewing gums, and lozenges
wherein said anticalculus agent has a mass average molecular weight of from about 3500 to about 7500 and M is an alkali metal, ammonium, or hydrogen.

2. An oral composition according to claim 1 wherein the amount of anticalculus agent is from about 2.5% to about 20%.

3. An oral composition according to claim 2 wherein the molecular weight of the anticalculus agent is from about 4000 to about 5500.

4. An oral composition according to claim 1 wherein the copolymer comprises acrylic acid and a monomer selected from the group consisting of methacrylic acid, 2 hydroxypropyl acrylate, 3-hydroxypropyl acrylate, 3-hydroxypropyl methacrylate, acrylamide and mixtures thereof.

5. An oral composition according to claim 4 in the form of a toothpaste.

6. An oral composition according to claim 5 which contains from about 3% to about 10% of the anticalculus agent.

7. An oral composition according to claim 6 wherein the anticalculus agent is a polyacrylic acid polymer having a molecular weight of from about 4300 to about 5200.

8. An oral composition according to claim 7 which contains a silica dental abrasive.

9. An oral composition according to claim 8 which in addition contains a soluble fluoride source.

10. An oral composition according to claim 1 in the form of a mouthwash.

11. An oral composition according to claim 10 wherein the amount of anticalculus agent is from 2.5% to about 20%.

12. An oral composition according to claim 11 wherein the molecular weight of the anticalculus agent is from about 4000 to about 5500.

13. An oral composition according to claim 12 wherein the anticalculus agent is a polyacrylic acid polymer.

14. An oral compositon according to claim 1 which is in the form of a lozenge.

15. An oral composition according to claim 1 which is in the form of a chewing gum.

* * * * *